United States Patent
White

(10) Patent No.: US 11,744,554 B2
(45) Date of Patent: Sep. 5, 2023

(54) SYSTEMS AND METHODS OF DETERMINING DIMENSIONS OF STRUCTURES IN MEDICAL IMAGES

(71) Applicant: FUJIFILM SonoSite, Inc., Bothell, WA (US)

(72) Inventor: Christopher A. White, North Vancouver (CA)

(73) Assignee: FUJIFILM SonoSite, Inc., Bothell, WA (US)

( * ) Notice: Subject to any disclaimer, the term of this patent is extended or adjusted under 35 U.S.C. 154(b) by 623 days.

(21) Appl. No.: 15/594,433

(22) Filed: May 12, 2017

(65) Prior Publication Data
US 2017/0325783 A1 Nov. 16, 2017

Related U.S. Application Data

(60) Provisional application No. 62/335,624, filed on May 12, 2016.

(51) Int. Cl.
*A61B 8/00* (2006.01)
*A61B 8/08* (2006.01)
(Continued)

(52) U.S. Cl.
CPC ............ *A61B 8/469* (2013.01); *A61B 8/0883* (2013.01); *A61B 8/4483* (2013.01); *A61B 8/461* (2013.01); *A61B 8/5207* (2013.01); *A61B 8/5223* (2013.01); *G06T 7/12* (2017.01); *G06T 7/0016* (2013.01); *G06T 2207/10132* (2013.01); *G06T 2207/20104* (2013.01); *G06T 2207/30048* (2013.01)

(58) Field of Classification Search
CPC ............... A61B 8/00; A61B 8/52; A61B 6/52
See application file for complete search history.

(56) References Cited

U.S. PATENT DOCUMENTS

| | | | |
|---|---|---|---|
| 6,193,660 B1 * | 2/2001 | Jackson | A61B 8/00 600/443 |
| 6,381,350 B1 * | 4/2002 | Klingensmith | G06T 7/149 382/128 |

(Continued)

FOREIGN PATENT DOCUMENTS

| | | |
|---|---|---|
| JP | 2002-224116 A | 8/2002 |
| JP | 2009-011468 A | 1/2009 |

(Continued)

OTHER PUBLICATIONS

Tsuyoshi; Machine Translation of JP 4536419 B2, Hitachi Medical Corporation, Sep. 1, 2010 (Abstract, drawings, and Japanese language version were supplied by Applicant in IDS Aug. 1, 2017) (Year: 2010).*

(Continued)

*Primary Examiner* — James M Kish
(74) *Attorney, Agent, or Firm* — Colby Nipper PLLC

(57) ABSTRACT

Systems and methods for producing ultrasound images are disclosed herein. In one embodiment, ultrasound image data are acquired in discrete time increments at one or more positions relative to a subject. Control points are added by a user for two or more image frames and a processor interpolates the location of the control points for image frames obtained at in-between times.

20 Claims, 15 Drawing Sheets

(51) Int. Cl.
  *G06T 7/12* (2017.01)
  *G06T 7/00* (2017.01)

(56) References Cited

U.S. PATENT DOCUMENTS

| | | | |
|---|---|---|---|
| 2002/0102023 A1* | 8/2002 | Yamauchi | G06F 19/00 382/199 |
| 2004/0015081 A1* | 1/2004 | Kramer | A61B 8/08 607/9 |
| 2006/0241461 A1 | 10/2006 | White et al. | |
| 2007/0066898 A1* | 3/2007 | Hendriks | A61B 5/021 600/437 |
| 2007/0255136 A1 | 11/2007 | Kristofferson et al. | |
| 2008/0114244 A1* | 5/2008 | Murashita | A61B 8/483 600/443 |
| 2009/0012397 A1 | 1/2009 | Matsushita | |
| 2009/0131788 A1* | 5/2009 | Settlemier | A61B 8/0858 600/438 |
| 2010/0130862 A1 | 5/2010 | Yoo | |
| 2011/0190633 A1* | 8/2011 | Kawagishi | G06T 7/00 600/443 |
| 2016/0055650 A1 | 2/2016 | Park et al. | |

FOREIGN PATENT DOCUMENTS

| | | |
|---|---|---|
| JP | 4536419 B2 | 9/2010 |
| JP | 2013-000414 A | 1/2013 |
| JP | 2013-135942 A | 7/2013 |
| JP | 2015-226711 A | 12/2015 |

OTHER PUBLICATIONS

International Searching Authority, International Search Report and Written Opinion, PCT Application PCT/US2017/032539, dated Jul. 14, 2017, 12 pages.

"Introduction to Vascular Ultrasonography, (U.S.) Polak, P. Beijing: People's Military Medical Publishing House, Feb. 2015, 6th edition, pp. 29-34", pp. 31-32 [Chinese and English versions provided].

"Solid Modeling Technology," Chunmei Ouyang, et al., National Defense Industry Press, Nov. 1991, 1st edition, pp. 123-126) [Unavailable, please see Chinese Third OA p. 4].

Translation of Chinese Third Office Action dated Sep. 6, 2021 in CN Application No. 201780029145.6.

* cited by examiner

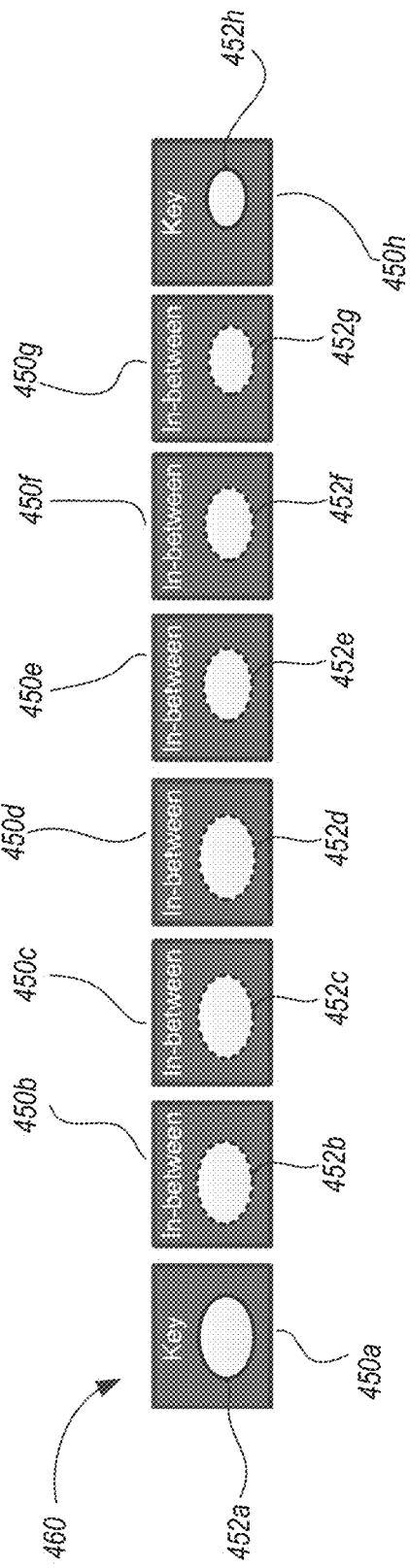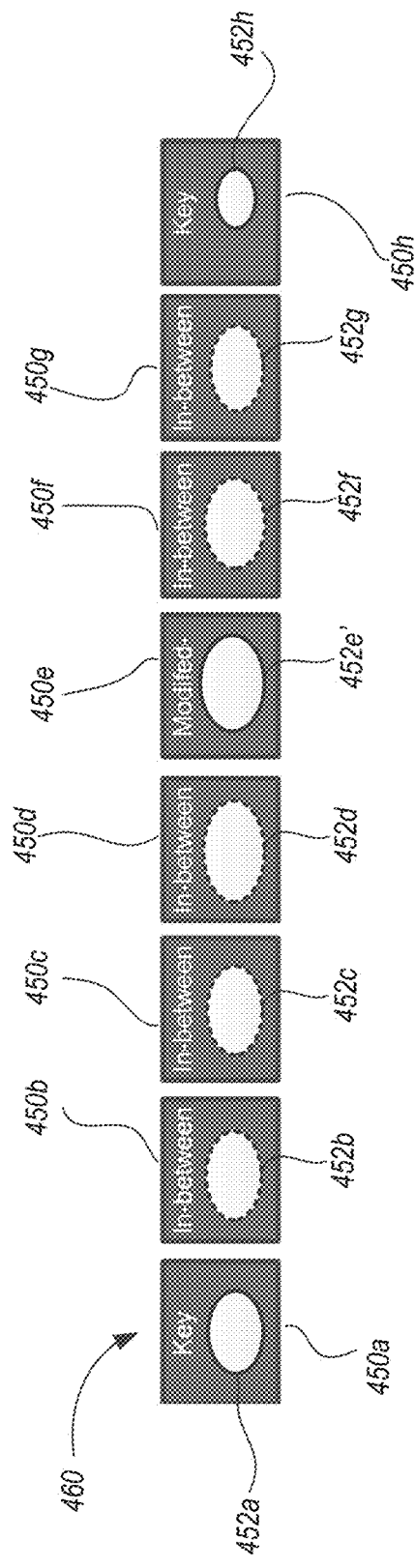

SYSTEMS AND METHODS OF DETERMINING DIMENSIONS OF STRUCTURES IN MEDICAL IMAGES

RELATED PRIORITY APPLICATION

The present application claims the benefit of and priority, to U.S. Provisional Patent Application 62/335,624 filed May 12, 2016, which in herein incorporated by reference in its entirety.

PATENTS AND PATENT APPLICATIONS INCORPORATED BY REFERENCE

The following patents and publications are incorporated herein by reference in their entireties: U.S. Pat. No. 7,052,460, titled "SYSTEM FOR PRODUCING AN ULTRASOUND IMAGE USING LINE-BASED IMAGE RECONSTRUCTION," and filed Dec. 15, 2003; U.S. Pat. No. 7,255,678, titled "HIGH FREQUENCY, HIGH FRAME-RATE ULTRASOUND IMAGING SYSTEM," and filed Oct. 10, 2003; U.S. Pat. No. 7,901,358, titled "HIGH FREQUENCY ARRAY ULTRASOUND SYSTEM," and filed Nov. 2, 2006; U.S. Pat. No. 8,317,714, titled "SYSTEMS AND METHODS FOR CAPTURE AND DISPLAY OF BLOOD PRESSURE AND ULTRASOUND DATA," and filed Nov. 27, 2012; and U.S. Patent Publication No. 2014/0128738, titled "Systems and methods for forming ultrasound images," and filed Nov. 5, 2013.

TECHNICAL FIELD

The present disclosure is generally directed to medical imaging systems. Embodiments of the present disclosure are directed to using ultrasound imaging systems to determine boundaries and dimensions of anatomical structures in one or more ultrasound images.

BRIEF DESCRIPTION OF THE DRAWINGS

FIGS. 4A and 4B are schematic diagrams illustrating user input of the boundaries of an anatomical structure.

DETAILED DESCRIPTION

Figure 1:
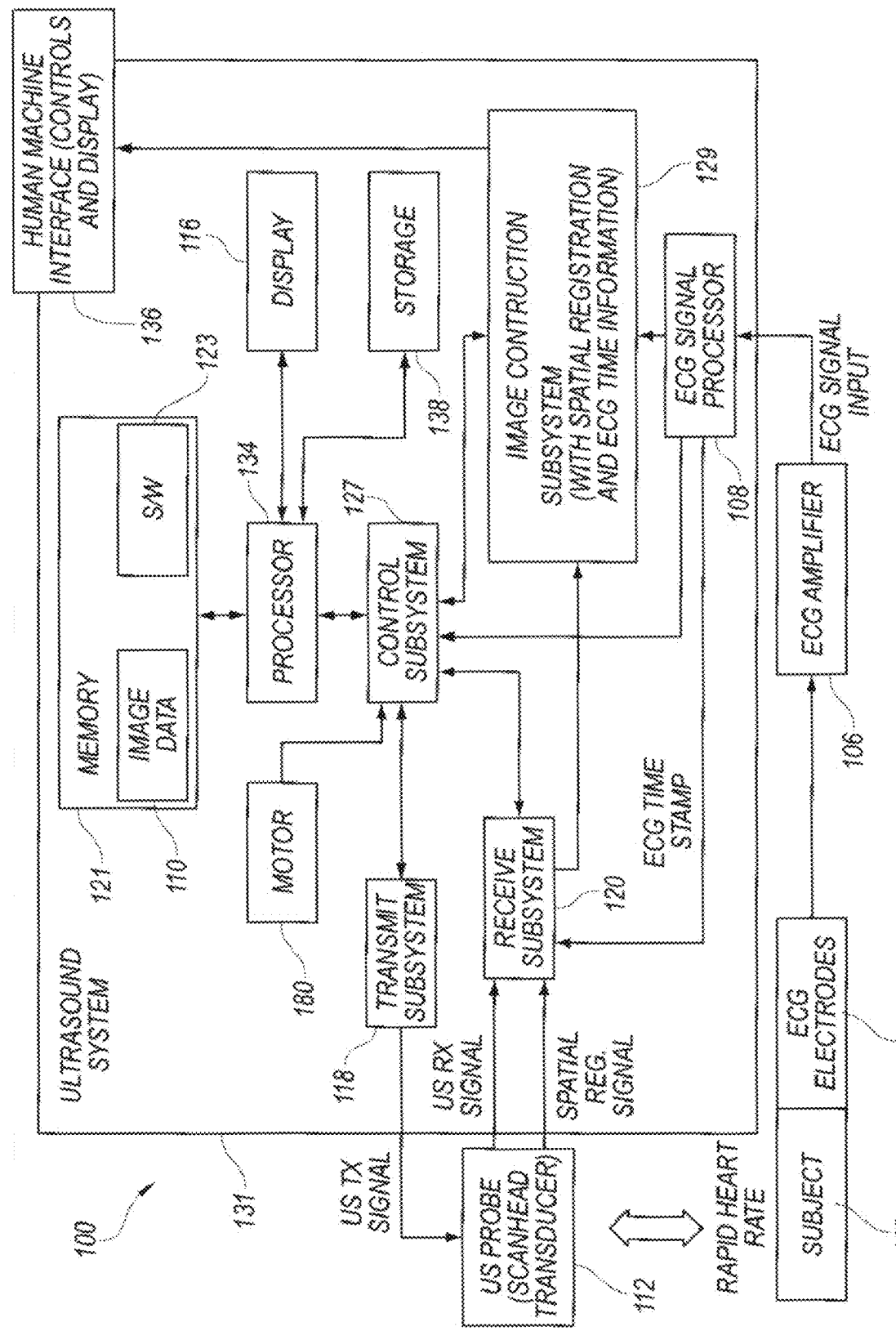
FIG. 1 is a block diagram of an ultrasound imaging system configured in accordance with embodiments of the disclosed technology.

In ultrasound imaging devices, images of a subject are created by transmitting one or more acoustic pulses into the body from a transducer. Reflected echo signals that are created in response to the pulses are detected by the same or a different transducer. The echo signals cause the transducer elements to produce electronic signals that are analyzed by the ultrasound system in order to create a map of some characteristic of the echo signals such as their amplitude, power, phase or frequency shift etc. The map can be used to form a two-dimension (2D) image.

Multiple 2D images formed using ultrasound echo signals received from the subject at different positions can be used to form a three-dimensional (3D) image of the subject. Several 3D images of the subject acquired at different times and/or during different portions of the subject's cardiac or respiratory cycle can be used to form a four-dimensional (4D) image (e.g., a video and/or cineloop) of the subject. An operator can use 3D and/or 4D image sets to determine a volume of a structure (e.g., a heart and/or another organ or structure) in the images. Operators may wish to measure, for example, a volume of a heart at a particular time point and/or multiple time points. Determining the volume of the heart typically involves tracing a boundary of a wall of the heart in each of several 2D images. The traced boundaries can be used to form a 3D mesh describing the heart volume, and a dimension (e.g., a volume or surface area) of the heart can be calculated using the 3D mesh. For a 4D image set composed of several 3D images, however, tracing an outline of the structure in the individual 2D image frames of each 3D image can be time consuming and tedious. If, for example, a 3D image includes 20 2D image frames, a 4D image made from 20 3D images, for example, the total data set can include 400 individual image frames. Some prior art methods attempt to trace structures in images automatically using segmentation, image analysis and/or other automatic tracing means. In many high frequency ultrasound images, however, border definitions of structures can be very unclear and thus automated analysis can be challenging and inaccurate. An operator with an understanding of the anatomy of an organ therefore may more accurately discern where a boundary in an image should be drawn.

Embodiments of the disclosed technology can reduce the amount of operator input needed to determine boundaries of anatomical structures in 3D and/or 4D ultrasound image sets, which can include dozens, hundreds or even thousands of images. In one embodiment, for example, a method of operating an ultrasound imaging system to determine a dimension of a region of interest in a subject includes acquiring ultrasound echo data from the subject using a transducer coupled to the ultrasound imaging system. The ultrasound echo data can be acquired at a plurality of times and at a plurality of positions relative to the region of interest. The method further includes constructing, with the ultrasound imaging system, a plurality of 3D images of the region of interest using the acquired ultrasound echo data. The individual 3D images can include a plurality of image frames and the individual image frames can be acquired at one of the plurality of positions and at one of the plurality of times. The ultrasound imaging system receives manual input that can include, for example, user-selected points in a first image frame that define an anatomical boundary in the region of interest. The imaging system can compute an anatomical boundary in the region of interest in a second image frame based on the user-selected points in the first image frame. In some aspects, the first and second image frames include ultrasound data acquired at the same time but different positions. In other aspects, however, the first frame includes data acquired at the same position and a different time as the second frame. The system can determine the dimension (e.g., a volume or a surface area) of the region of interest using the user-defined boundary in the first image frame and the computed boundary in the second image frame and can output the dimension of the region of interest to a display coupled to the ultrasound imaging system.

Suitable System

FIG. 1 is a block diagram illustrating an imaging system 100. The system 100 operates on a subject 102. An ultrasound probe 112 proximate to the subject 102 is configured to acquire image information. The ultrasound probe generates ultrasound energy at high frequencies, such as, but not limited to, center frequencies between 15-60 MHz and higher. Further, ultrasound operating frequencies significantly greater than those mentioned above can be used. The subject 102 is connected to electrocardiogram (ECG) electrodes 104 to obtain a cardiac rhythm from the subject 102. The electrodes 104 transmit the cardiac signal to an ECG amplifier 106 to condition the signal for provision to an ultrasound system 131. It is recognized that a signal processor or other such device may be used instead of an ECG amplifier to condition the signal. If the cardiac signal from the electrodes 104 is suitable, then use of an amplifier 106 or signal processor could be avoided entirely.

The ultrasound system 131 includes a control subsystem 127, an image construction subsystem 129, sometimes referred to as a "scan converter", a transmit subsystem 118, a receive subsystem 120 and a human-machine interface 136 (e.g., a user interface and/or a user input). A processor 134 is coupled to the control subsystem 127 and the display 116 is coupled to the processor 134. A memory 121 is coupled to the processor 134. The memory 121 can be any type of computer memory, and is typically referred to as random access memory "RAM," in which the software 123 is stored. The software 123 controls the acquisition, processing and display of the ultrasound data allowing the ultrasound system 131 to display a high frame rate image so that movement of a rapidly moving structure may be imaged. The software 123 comprises one or more modules to acquire, process, and display data from the ultrasound system 131. The software comprises various modules of machine code, which coordinate the ultrasound subsystems, as will be described below. Data is acquired from the ultrasound system, processed to form complete images, and then displayed to the user on a display 116. The software 123 allows the management of multiple acquisition sessions and the saving and loading of these sessions. Post processing of the ultrasound data is also enabled through the software 123.

The system for producing an ultrasound image using line-based image reconstruction can be implemented using a combination of hardware and software. The hardware implementation of the system for producing an ultrasound image using line-based image reconstruction can include any or a combination of the following technologies, which are all well known in the art: discrete electronic components, discrete logic circuit(s) having logic gates for implementing logic functions upon data signals, an application specific integrated circuit having appropriate logic gates, a programmable gate array(s) (PGA), a field programmable gate array (FPGA), one or more massively parallel processors, etc.

The software for the system for producing an ultrasound image using line-based image reconstruction comprises an ordered listing of executable instructions for implementing logical functions, and can be embodied in any computer readable medium for use by, or in connection with, an instruction execution system, apparatus, or device, such as a computer-based system, processor-containing system, or other system that can fetch and execute the instructions.

In the context of this document, a "non-transitory computer-readable medium" can be any physical means that can contain, store or transport the program for use by or in connection with the instruction execution system, apparatus, or device. The non-transitory computer readable medium can be, for example but not limited to, an electronic, magnetic, optical, electromagnetic, infrared, or semiconductor system, apparatus, or device. More specific examples (a non-exhaustive list) of the non-transitory computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CD-ROM) (optical).

The memory 121 can store the image data 110 obtained by the ultrasound system 100. A non-transitory computer readable storage medium 138 is coupled to the processor for providing instructions to the processor to instruct and/or configure processor to perform steps or algorithms related to the operation of the ultrasound system 131, as further explained below.

The ultrasound system 131 can include a control subsystem 127 to direct operation of various components of the ultrasound system 131. The control subsystem 127 and related components may be provided as software for instructing a general purpose processor or as specialized electronics in a hardware implementation. The ultrasound system 131 includes an image construction subsystem 129 for converting the electrical signals generated by the received ultrasound echoes to data that can be manipulated by the processor 134 and that can be rendered into an image on the display 116. The control subsystem 127 is connected to a transmit subsystem 118 to provide an ultrasound transmit signal to the ultrasound probe 112. The ultrasound probe 112 in turn provides an ultrasound receive signal to a receive subsystem 120. The receive subsystem 120 also provides signals representative of the received signals to the image construction subsystem 129. The receive subsystem 120 is also connected to the control subsystem 127. The scan converter is directed by the control subsystem 127 to operate on the received data to render an image for display using the image data 110.

The ultrasound system 131 can include an ECG signal processor 108 configured to receive signals from the ECG amplifier 106. The ECG signal processor 108 provides various signals to the control subsystem 127. In some embodiments, the receive subsystem 120 also receives an ECG time stamp from the ECG signal processor 108. The receive subsystem 120 is connected to the control subsystem 127 and an image construction subsystem 129. The image construction subsystem 129 is directed by the control subsystem 127.

The ultrasound system 131 can further include a motor 180 (e.g., a stepper motor, servo-torque motor, wobbler, etc.) configured to move the ultrasound probe 112. The motor 180, for example, can be configured to move the ultrasound probe 112 in one or more spatial directions (e.g., along an x, y and/or z-axis) and/or rotate the ultrasound probe 112.

The ultrasound system 131 transmits and receives ultrasound data through the ultrasound probe 112, provides an interface to a user to control the operational parameters of the imaging system 100, and processes data appropriate to formulate still and moving images that represent anatomy and/or physiology. Images are presented to the user through the interface display 116.

The human-machine interface 136 of the ultrasound system 131 takes input from the user, and translates such input to control the operation of the ultrasound probe 106. The human-machine interface 136 also presents processed images and data to the user through the display 116.

The software 123 in cooperation with the image construction subsystem 129 operate on the electrical signals developed by the receive subsystem 120 to develop a high frame-rate ultrasound image that can be used to image rapidly moving anatomy of the subject 102.

The control subsystem 127 coordinates the operation of the ultrasound probe 112, based on user selected parameters, and other system inputs. For example, the control subsystem 127 ensures that data are acquired at each spatial location, and for each time window relative to the ECG signal. Therefore, a full data set includes raw data for each time window along the ECG signal, and for each spatial portion of the image frame. It is recognized that an incomplete data set may be used with appropriate interpolation between the values in the incomplete data set being used to approximate the complete data set.

The transmit subsystem 118 generates ultrasound pulses based on user selected parameters. The ultrasound pulses are sequenced appropriately by the control subsystem 127 and are applied to the probe 112 for transmission toward the subject 102.

The receive subsystem 120 records the echo data returning from the subject 102, and processes the ultrasound echo data based on user selected parameters. The receive subsystem 120 also receives a spatial registration signal from the probe 112 and provides position and timing information related to the received data to the image construction subsystem 129.

Suitable Methods

Figure 2:
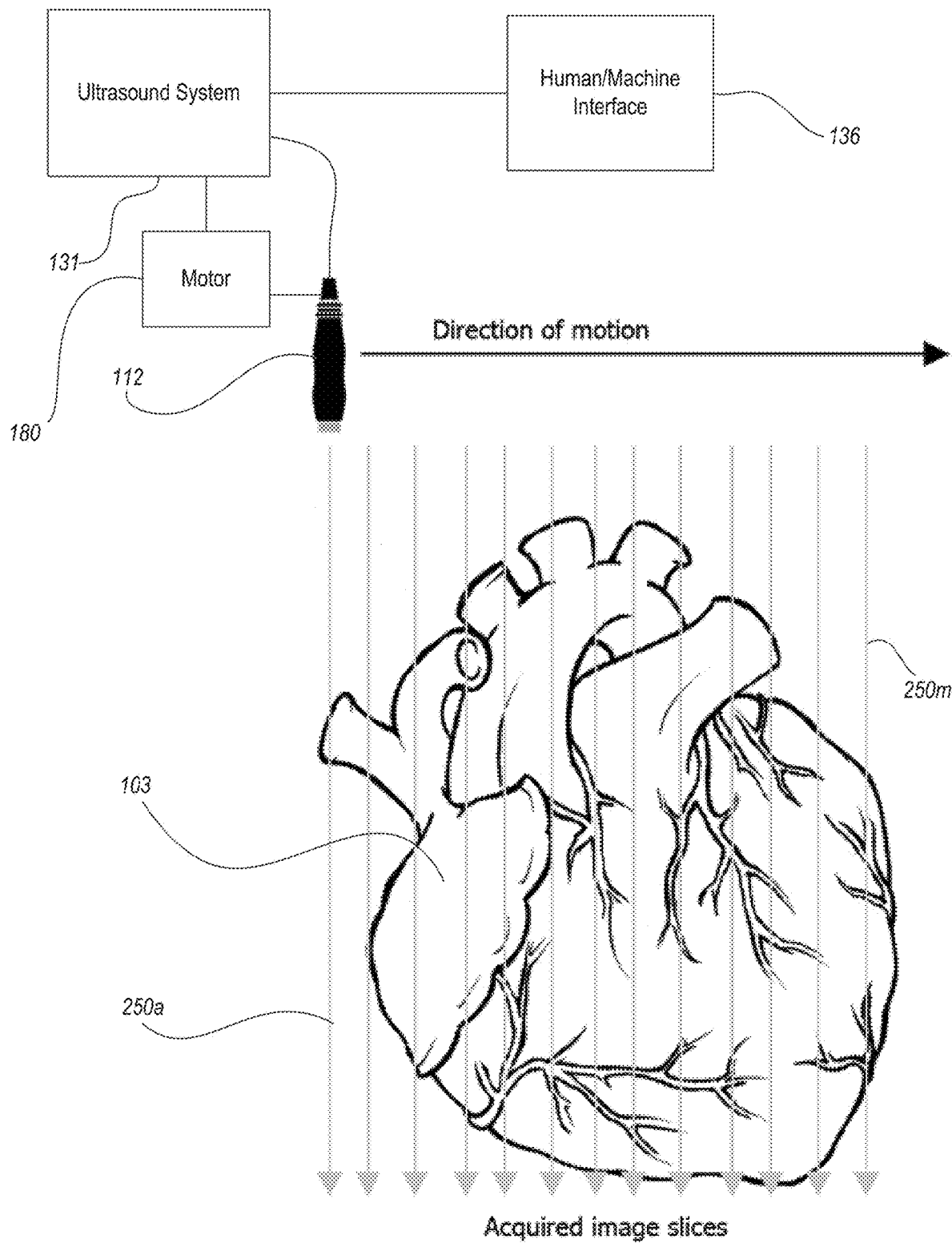
FIG. 2 is a schematic view of an exemplary ultrasound image acquisition in accordance with an embodiment of the disclosed technology.

FIG. 2 is a schematic view of an ultrasound image acquisition in accordance with an embodiment of the disclosed technology. The ultrasound probe 112 transmits and receives ultrasound energy into a region of interest 103 (e.g., a heart and/or another organ in a subject). The motor 180 moves the ultrasound probe 112 to each of a plurality of positions relative to the region of interest 103 that are spaced apart by a predetermined distance (e.g., 0.1 mm, 0.25 mm, 0.5 mm). The ultrasound system 131 receives signals from the ultrasound probe 112 corresponding to the transmitted ultrasound energy and forms a plurality of two-dimensional (2D) ultrasound image frames or slices 250a-250n of the region of interest 103. As described in more detail below in reference to FIGS. 3A-3C, the ultrasound image frames 250a-250n can be presented to the user at the interface 136 as a plurality of 2D images and/or can be used to form a three-dimensional (3D) image of the region of interest 103.

Figure 3A:
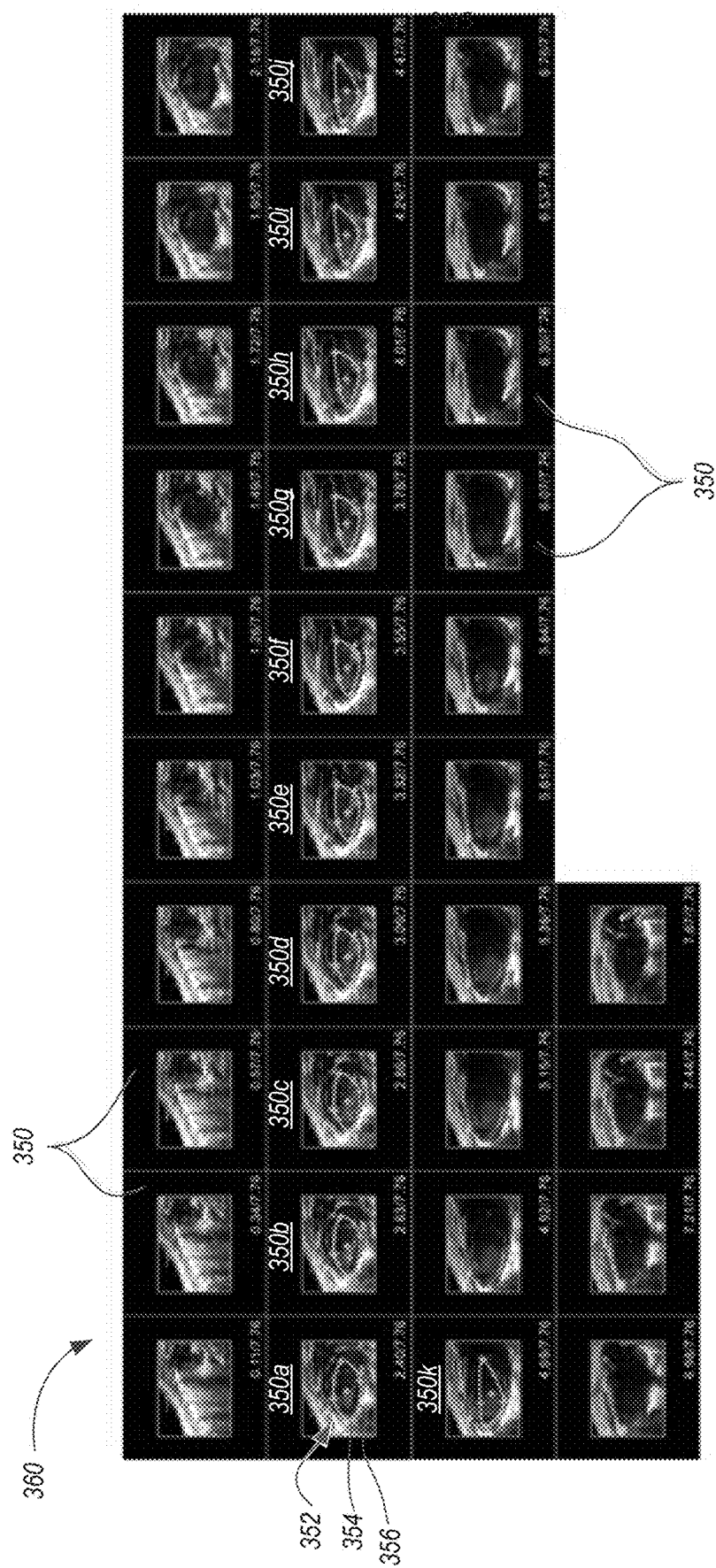
FIG. 3A is a screenshot of a set of ultrasound frames acquired using an embodiment of the disclosed technology.
Figure 3B:
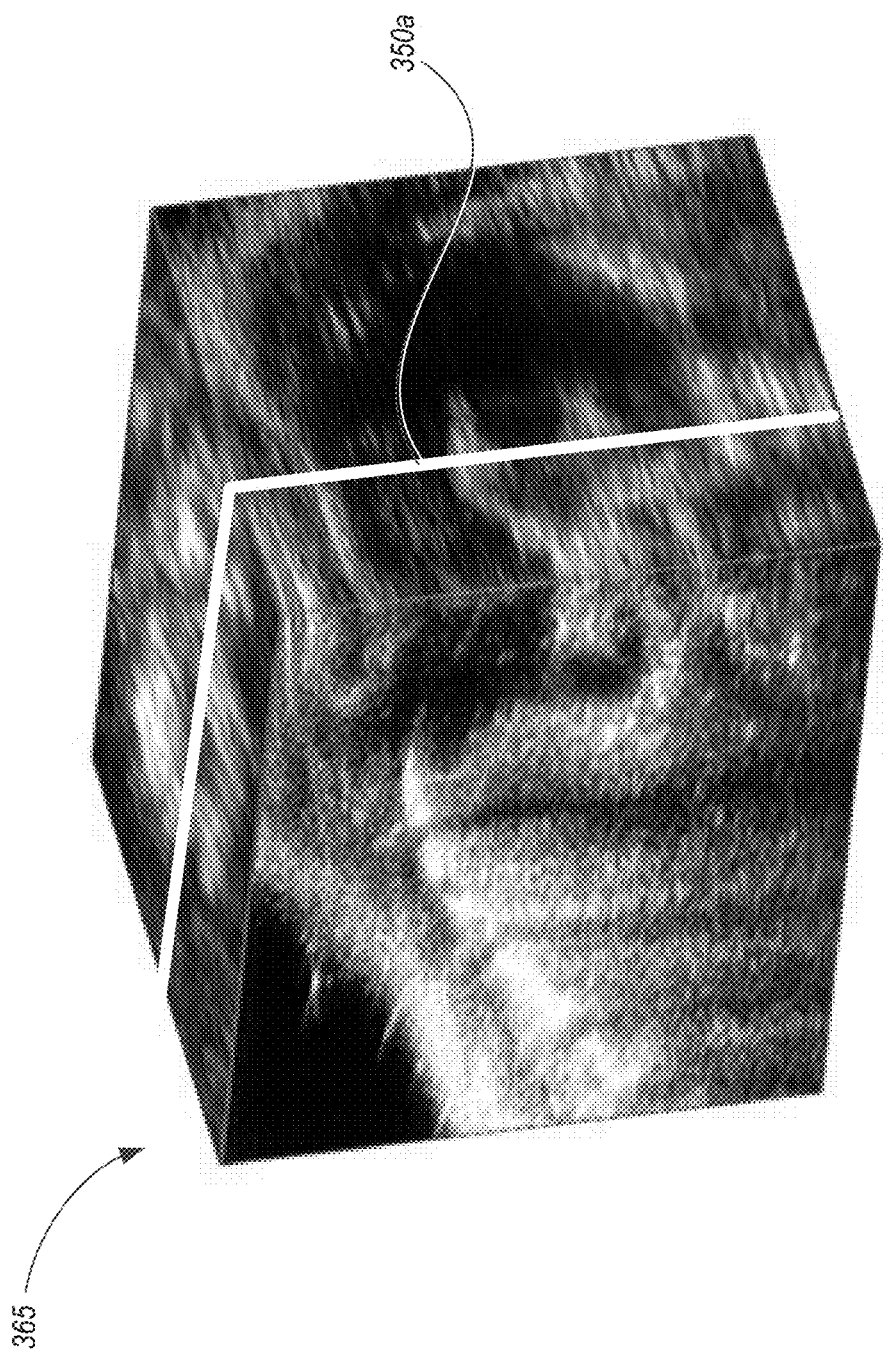
FIG. 3B is a 3D ultrasound image constructed in accordance with an embodiment of the disclosed technology.
Figure 3C:
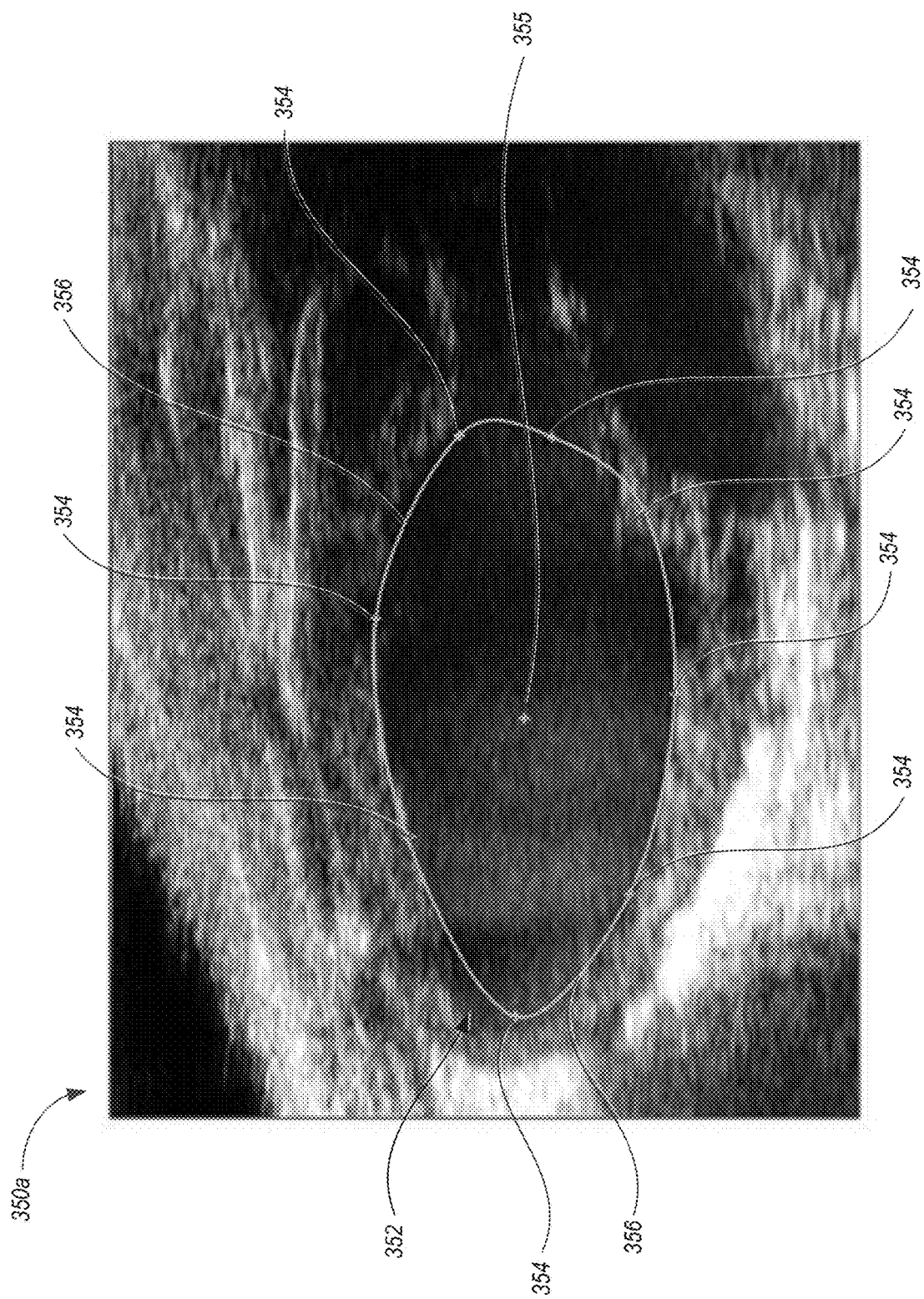
FIG. 3C is a single two-dimensional ultrasound image frame used in constructing the 3D ultrasound image of FIG. 3B.

FIG. 3A is a screenshot of an image set 360 comprising a plurality of ultrasound frames 350 acquired and constructed, for example, with the probe 112 and the ultrasound system 131 (FIGS. 1 and 2). FIG. 3B is a 3D ultrasound image 365 constructed by the system 131 using one or more of the ultrasound frames 350 of FIG. 3A, including an ultrasound image frame 350a. FIG. 3C is an enlarged view of the ultrasound image frame 350a.

Referring to FIG. 3A, the plurality of ultrasound image frames 350 are formed using ultrasound data acquired at a plurality of positions relative to the region of interest of a subject (as shown, for example, in FIG. 2). The ultrasound system 131 presents the image set 360 to a user. The user can select one or more image frames 350 and input information related to an edge, periphery or boundary of an anatomical structure (e.g., an organ such as a heart, liver, kidney, lung and/or a portion thereof) in at least one of the image frames 350. The user input may include manual input via a touchscreen, keyboard, mouse, touchpad, etc. FIG. 3A shows traced ultrasound image frames 350a-k each including a boundary 352 corresponding to edge or outline of an anatomical structure. As will be explained in further detail below in some embodiments of the disclosed technology, the ultrasound system 131 receives user input related only to the boundary 352 in the image frames 350a and 350k and the system generates boundaries in the intervening image frames 350b-j. In other embodiments, however, the system 131 receives user input related to the boundary 352 in each of the image frames 350a-k.

Referring now to FIGS. 3A and 3C together, each boundary 352 includes a plurality of control points 354 that are input by the user. For example, the user might input 3-6 control points or in some cases more as required depending on the complexity of the anatomy being traced. More complex shapes will require more user input. The ultrasound system 131 connects adjacent control points 354 with a plurality of segments 356 and in one embodiment, calculates an approximate center point 355 of the control points 354. In the illustrated embodiment of FIG. 3C, the segments 356 comprise cubic splines between adjacent control points 354. Allowing the user to draw or input the relatively few control points 354 along the boundary 352 of an anatomical structure (e.g., a heart wall) and joining the control points with smoothly connected cubic spline segments can significantly reduce the amount of time spent by the user defining the boundaries of the anatomical structure in one or more images. Moreover, the cubic splines have a curve-like shape which can be naturally very consistent with curves along the anatomical structures such as, for example, a heart wall. In some embodiments, however, the segments 356 may be linear and/or have shapes different from a cubic spline. In other embodiments, the system 131 may receive user input that includes an entire traced outline of the anatomical structure. The system 131 can determine a dimension (e.g., a volume and/or a surface area) defined by the boundaries 352 in the image frames 350a-k using, for example, software stored on the memory 121 (FIG. 1). Examples of one or more techniques for determining a dimension of an anatomical structure can be found, for example, in U.S. Pat. No. 8,317,714 incorporated by reference above.

FIGS. 4A and 4B are diagrams illustrating user input and boundary generation in accordance with an embodiment of the disclosed technology. Referring to FIG. 4A, an image set 460 includes a plurality of image frames 450a-h (e.g., the image frames 350a-h of FIG. 3A) shown schematically without ultrasound data for clarity and ease of understanding. The image frames 450a-h include one or more so-called "key" frames 450a and 450h and several in-between frames 450b-g. In accordance with one embodiment, a user inputs control points over one or more anatomical structures shown in the key frame 450a and an imaging system (e.g., the ultrasound system of FIG. 1) draws a boundary 452a. The user repeats the sequence for the key frame 450h and the imaging system draws a boundary 452h. The system then generates a set of boundaries 452b-g in the in-between frames 450b-g by interpolating between the boundaries 452a and 452h.

In one embodiment, the user is not manipulating the underlying ultrasound data shown in each of the frames. Rather, the user is inputting a number of data points that define a shape that is separate from the underlying ultrasound data. The ultrasound system 131 determines intermediate shapes between those that are input by the user and uses the input and determined shapes to calculate volumes, surface areas etc.

Referring to FIG. 4B, the user can modify the control points placed over an image frame 450e by inputting additional control points or moving the control points along a boundary 452e'. The ultrasound system therefore computes a new boundary from the modified control points. The ultrasound system then performs a re-interpolation of the boundaries 452b-d for the in-between frame using the boundary 452a and the modified boundary 452e' as well as the boundaries 452f and 452g. Using the modified boundary 452e' and the user input boundary 452h, the accuracy of the boundaries in the in-between frames 452b-d, 452f and 452g is increased without user input in the in-between frames.

Figure 5A:
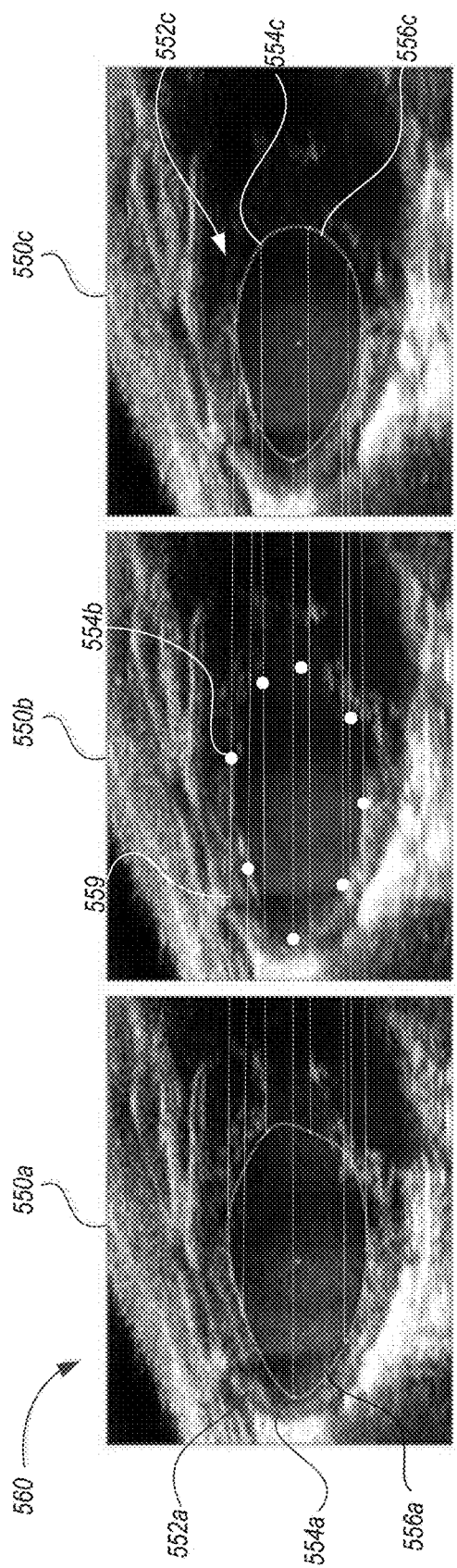
FIGS. 5A and 5B are partially schematic diagrams illustrating interpolation methods in accordance with an embodiment of the disclosed technology.

FIG. 5A is a diagram illustrating the generation of boundaries of anatomical structures in accordance with an embodiment of the disclosed technology. FIG. 5A shows an image set 560 comprising key frames 550a and 550c over which a user has placed control points to define boundaries 552a and 552c that trace a heart wall. As described above in reference to FIGS. 3A-4B, the user inputs one or more control points 554 (numbered in the frames 550a-c as control points 554a-c) over the key frames 550a and 550c. A plurality of segments 556 (e.g., cubic splines) connect adjacent control points 554 in the individual key frames 550a and 550c. The system (e.g., the system 131 of FIG. 1) can automatically generate control points 554b for the in-between frame 550b by interpolation and/or morphing along lines 559 to define the control points for the in-between frames.

As in traditional key frame animation, a bounding pair of frames define the key frames. The interior, or 'in-between' frames may only include only a slight modification of the outer frames. For example, a heart wall boundary on the in-between frames may be sufficiently approximated using the information present in the key frames. The in-between frame traces can be morphed based on their proximity to the traces defined by the user. In some embodiments, all the walls of the heart may be successfully traced from control points placed over only a few 'key' frames drawn by the user. The traces on the other frames can be morphed or interpolated representations of the boundaries in these key frames. As the user adjusts the control points on the key frames, the control points for some or all of the in-between frames may be automatically adjusted based on the updated information. As discussed above, the user can adjust control points in the in-between frames that he or she deems not lying on or near a boundary of the heart wall. This additional information is then applied to the entire data set to improve the quality of the remaining in-between frames.

Figure 5B:
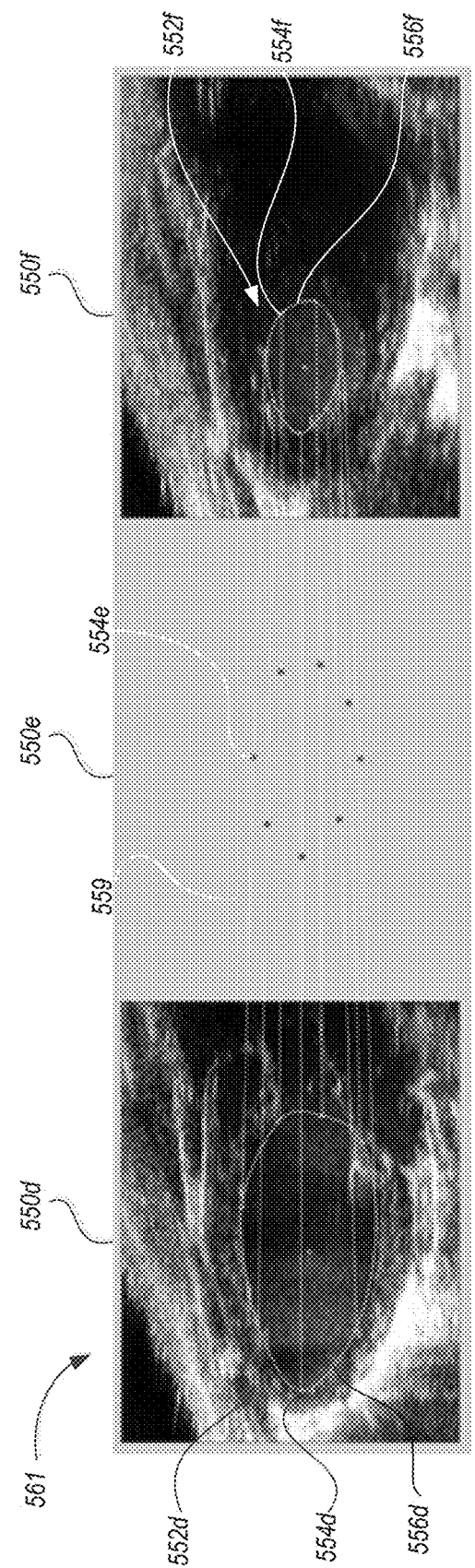

FIG. 5B is a diagram illustrating the generation of boundaries of anatomical structures in accordance with another embodiment of the disclosed technology. An image set 561 includes key frames 550d and 550f having corresponding control points placed over the image frame that define boundaries 552d and 552f that represent a heart wall. In the illustrated embodiment, the boundaries 552d and 552f have substantially the same shape but different sizes. Rather than the user inputting a completely new set of control points over an in-between frame, the system can automatically generate control points 554e by interpolating between control points 554d in the key frame 550d and control points 554f in the key frame 550f. In some instances, for example, it is faster to resize or move the entire boundary. The system can copy the control points and connecting splines for the boundary shape from either of the key frames and allow the user to simply enlarge or contract the boundary size for the in-between frame without changing its shape. In some embodiments, the boundary can also be rotated and/or shifted to a new position without changing its size or shape.

Figure 6A:
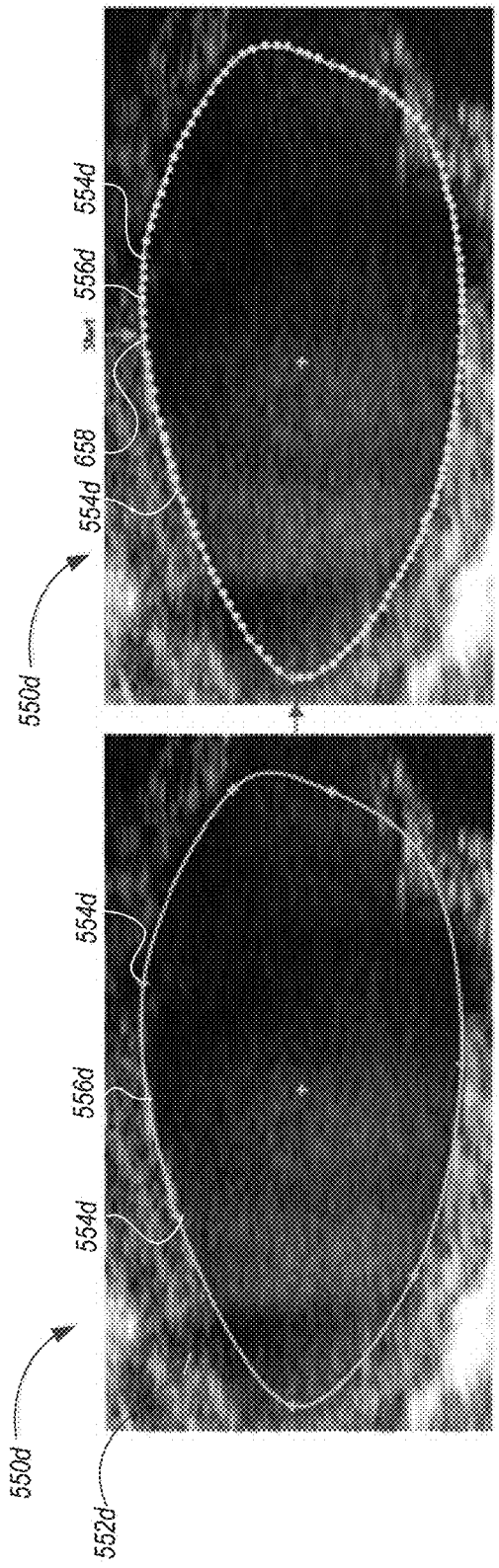
FIGS. 6A and 6B are partially schematic diagrams illustrating another interpolation method in accordance with an embodiment of the disclosed technology.
Figure 6B:
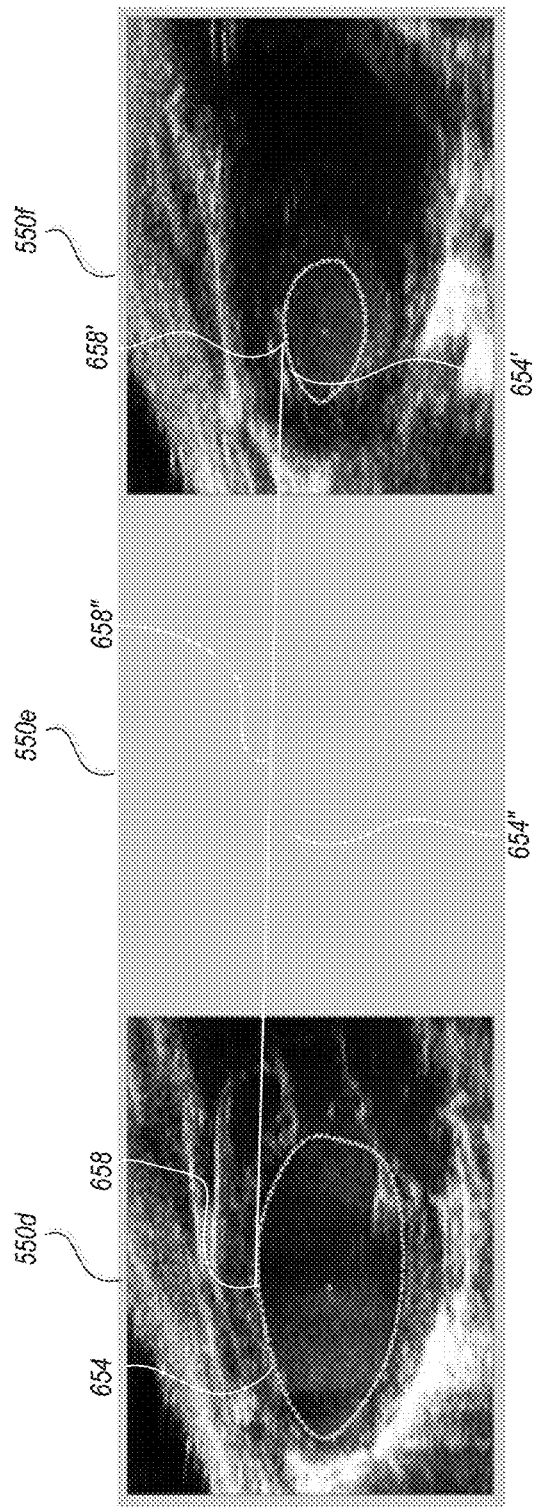

FIGS. 6A and 6B illustrate another interpolation method in accordance with an embodiment of the disclosed technology. Referring to FIGS. 6A and 6B together, the system generates a number (e.g., 128, 256, 512) of points 658 along the splines 556 between adjacent control points 554. User interaction is simplified by only presenting and allowing user modification of control points. For example, the original boundary points as entered by the user are control points. The user may enter for example, 3, 4, 5 or any number of control points. The system then generates internal points 658 which are not presented to the user but used for internal calculations. In some embodiments, the indexing of the points 658 can start at the same rotational position along each of the splines 556. For example, the system can begin ordering with the point 658 at a 12 o'clock position (i.e., a 0° and/or vertical position as shown in the diagram) and continue to index additional points 658 in a clockwise and/or counterclockwise direction. The system can then select a matching pair of points from the left key frame 550d and the right key frame 550f (FIG. 6B). For example, from each point set 658 and 658' select the n'th point (i.e. the 16'th point). As shown in FIG. 6B, the point 658 in frame 550d is matched with a point 658' in frame 550f. Given a coordinate location of each point (horizontal and vertical, x, y, defined in mm), a parametric linear equation can be calculated between these matched points 658 and 658'. Using these equations and the position of the image frame 550e, the system selects a coordinate location for new point 658" on the in-between frame 550e. In some embodiments, position might be time, or frames. This is repeated for all of the calculated internal point pairs (for example, 128, 256, 512 point pairs). The result is a boundary representation 658" on frame 550e.

In some embodiments, a linear equation, e.g. $y=mx+b$, is used to calculate the points on the in-between frame 550e where the dependent variable x is frame position or time. For example, for each of the two spatial parameters of a point (horizontal and vertical position) a linear equation defined as $y=mx+b$ can be used to determine corresponding points for the in-between frame 550e using the values from the key frames 550d and 550f. In this equation, y is one of the spatial parameters (e.g., position) and x is the frame position, which can be measured, e.g., in units of frames (or time or position). To derive the physical position of the point for the in-between frame 550e, the linear equation defined can be used by inserting the variable x for the correct frame position. For example, referring to FIG. 6B, if control points are interpolated within a time point from control points 658 to 658', these points might be described with coordinates x, y, z where x is the horizontal position within the 2D image 550d, y is the vertical position within the 2D image 550d, and z describes the position of the image as acquired by the 3D motor. For example, control point 658 might be x, y, z (5.5 mm, 3.3 mm, 6 mm). Control point 658' might be (4.0 mm, 5.2 mm, and 8 mm). To interpolate the location of the control point 658" on frame 550e where the z position of this frame is 7 mm, the linear equations are solved for the two parameters as follows y=mz+b and x=mz+b. Thus the equation for x values is x=−0.75z+10.0 and the equation for y values is y=0.95 z−2.4, both as a function of z. Thus the point 658" is (4.75 mm, 4.25 mm, 7 mm). When interpolating across time points, then the z axis becomes time and the two points would be described x, y, t where t is in units of time. For example, the two points might be 658 (5.5 mm, 3.3 mm, 6 ms) and 658' (4.0 mm, 5.2 mm, and 8 ms). The linear equations are solved for the two parameters as follows y=mt+b and x=mt+b. Thus the equation for x values is x=−0.75t+10.0 and the equation for y values is y=0.95 t−2.4, both as a function of t. Thus, the interpolated control point 658" has values (4.75 mm, 4.25 mm, 7 ms). The process above repeats for all the point pairs from the key frames 550d and 550f. The result is that the points 658" for the in-between frame 550e will have a shape defined by the new points as shown in FIG. 6B.

In some embodiments, the internal points along the splines between the user defined control points can be interpolated for the in-between frames instead of using the user defined control points. Each frame may include several hundred points (e.g. 128, 256, 512 etc.) calculated along the splines. In one embodiment, each of the these points is numbered starting from a common position such as the 12 o'clock position. A mathematical line can be determined between all, or fewer than all, of these points on one key frame and the same numbered point on a second key frame to calculate a corresponding point in the in-between frame.

In order to reduce the number of interpolated points that are shown to the user for the in-between frame, the system determines which of the interpolated points corresponds most closely to the user determined control points in the key frames. For example, a user defined control point in one key frame might be closest to point 63 in one key frame while the corresponding user defined control point in the other key frame might be closest to point 75. If the number of control points in key frame 550d does not match the number in key frame 550f, additional control points can be calculated and inserted along at least one of the splines 658 or 658' such that they each contain the same number of control points. This new control point only exists for internal calculations and not be shown to the user. The same or similar linear interpolation described above can be used to calculate positions for a new control point index for the in-between frame 550e. For example, the linear equation for the system {63, 6 mm} and {75, 8 mm} is solved for in-between frame 550e, which exists at 7 mm. The equation of this system is Index=6x+27 where x is the position of the frame. Calculating for frame 550e at 7 mm, the index is thus 69. Therefore, interpolated point 69 is selected as a control point to show to the user for the in-between frame. This process is repeated for each pair of control points on key frames 550d and 550f. The result is a set of interpolated control points on frame 550e which are presented to the user and can be selected and modified.

In some embodiments, instead of using linear interpolation of points and control point indexes between two frames, cubic interpolation or even quadratic interpolation could be used. In this case, instead of using two bounding frames to solve the system three frames would be used in the case of cubic interpolation and four in the case of quadratic interpolation. Cubic spline interpolation could also be used which would use data from all the frames to generate data for the in-between frames.

Once the interpolated points are computed, they can be plotted on the in-between frame and splines calculated that connect the interpolated control points. The user can move the position of the calculated control points. If the position a control point is moved to better coincide with an anatomical feature, the in-between frame can then be designated as a key frame and the positions of the control points in the frame can be used as a basis for determining the positions of control points in other in-between frames. In some instances, for example, it is faster to resize or move the entire boundary, rather than modify individual control points. The user can enlarge or contract the boundary size for the in-between frame without changing its shape. In some embodiments, the boundary can also be rotated and/or shifted to a new position without changing its size or shape.

Figure 7:
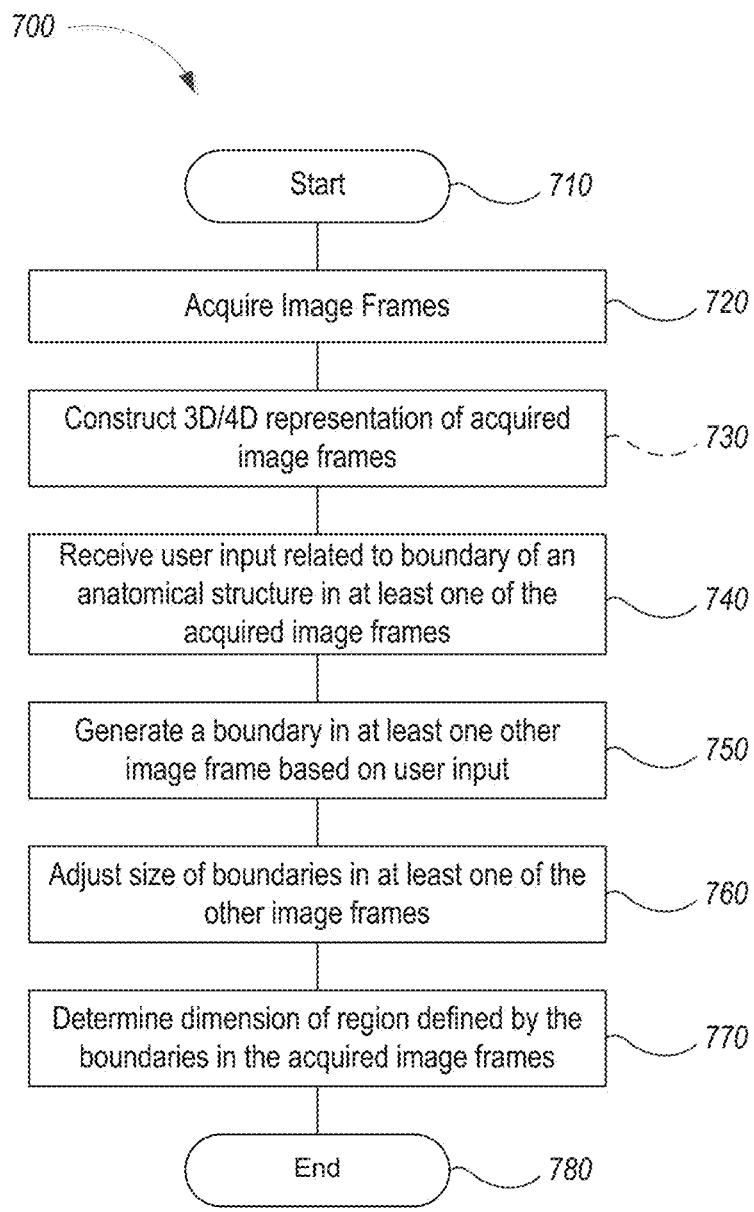
FIG. 7 is a flowchart of a process of generating boundaries of one or more anatomical structures in one or more ultrasound images in accordance with an embodiment of the disclosed technology.

FIG. 7 is a flowchart illustrating a process 700 of generating a boundary of one or more anatomical structures (e.g., heart, liver, kidney and/or one or more portions thereof) in one or more 2D ultrasound image frames. In some embodiments, instructions for causing a processor to implement the process 700 can be stored on a memory (e.g., the memory 121 of FIG. 1) and executed by the processor (e.g., the processor 134 of FIG. 1) of an ultrasound imaging system (e.g., the system 131 of FIG. 1). At block 710, the process 700 generates and transmits ultrasound energy (e.g., ultrasound energy having a center frequency greater than about 15 MHz) from an ultrasound transducer probe (e.g., the probe 112 of FIGS. 1 and 2) toward a region of interest (e.g., a heart, liver, kidney) in a subject (e.g., a human or an animal, such as a rat or a mouse). At block 720, the process 700 acquires ultrasound data corresponding to ultrasound echoes received from the subject and uses the acquired ultrasound data to form one or more ultrasound image frames (e.g., the image frames 350 of FIG. 3A). In some embodiments, the process 700 can acquire the image data at discrete positions relative to the region of interest. As described above, for example, in reference to FIG. 2, the process 700 can control a motor (e.g., the motor 180) and move the probe a predetermined incremental distances relative to the region of interest to acquire ultrasound data at a plurality of positions. In other embodiments, however, the process 700 acquires the ultrasound image data from the region of interest in a single data acquisition.

A block 730, the process 700 optionally constructs one or more 3D or 4D images using the image frames acquired at block 720. The process 700 can form a 3D image using a plurality of 2D image frames acquired at predetermined positions relative to the region of interest. The process 700 can also form one or more 4D images using, for example, several 3D images acquired at different portions of the subject cardiac cycle. In one embodiment, the process 700 constructs a 4D image using one or more methods disclosed in the applicant's co-pending application Ser. No. 14/072,755, published as U.S. Patent Publication No. 2014/0128738, and incorporated by reference above. In other embodiments, the process proceeds directly to block 740 without constructing 3D and/or 4D images.

At block 740, the process 700 presents the 2D image frames acquired at block 720 to an operator (e.g., the image set 360 of FIG. 3A). The operator selects one or more 2D image frames as key frames and places one or more points or markers as control points near and/or along a boundary of an anatomical structure in the individual image frames.

At block 750, the process 700 generates a boundary in one or more acquired image frames based on the user input received at block 740. As discussed above in reference to FIGS. 4A and 4B, for example, the user can select two key frames and trace or plot points around an anatomical boundary in the key frames. Splines or other mathematical curves/lines can be computed to connect the control points to trace the perimeter of the anatomical features. The process 700 can interpolate between individual control points in a first key frame and corresponding control points in a second key frame to automatically generate boundaries in one or more in-between image frames that are between the key frames.

At block 760, the process can present the 2D image frames with drawn boundaries to the user via a display for additional editing. As discussed above in reference in FIG. 4B, for example, the process 700 can receive user input for any of the generated boundaries to further increase accuracy of the boundaries. For example, the user can adjust a boundary generated in one of the in-between frames in which the generated boundary does not match up with a boundary of the anatomical structure in the image. Each in-between image that the user manually adjusts becomes a new key frame and therefore can improve the accuracy of the remaining in-between frames.

At block 770, the process 700 can determine a measurement (e.g., a surface area, circumference, volume) of a region defined by the manually-input and generated boundaries in the 2D image frames.

At block 780, the process 700 outputs the determined measurement(s) to the operator.

FIGS. 8A-8E are schematic diagrams illustrating the generation of boundaries of anatomical structures in a 4D image set 860 in accordance with some embodiments of the disclosed technology. In the figures, anatomy boundaries shown in solid lines are input by a user, while those shown in dashed lines are computed. Referring to FIGS. 8A-8E together, a 4D image set includes a plurality of 2D image frames of a region of interest arranged in a grid of rows and columns. The rows A-M represent 2D image slices taken at different positions relative to the region of interest as discussed above, for example, with reference to FIG. 2. The columns TP1-TP9 represent 2D images taken at different time points and/or periods of time. Taken together, the 2D image frames in each column can comprise a 3D image of the region of interest acquired at a particular time TP1-TP9. In some embodiments, the times TP1-TP9 correspond to different portions of the subject's cardiac cycle. TP1 can represent, for example, a first time point in the subject's heart cycle (0 ms time). TP5 can represent, for example, a time point approximately ½ way through the heart cycle. Depending on the heart rate, TP5 might be 50 ms (if the period of the heart cycle is 100 ms, for example). In some aspects, TP9 and TP1 can generally represent the same or similar time point in a cycle as the heart completes one cycle and begins a subsequent cycle. In some aspects, the data obtained at time points at the ¼ point (TP3) and the ¾ point (TP7) are similar.

In the illustrated embodiment, the 4D image set includes 2D image frames acquired at 13 positions and 9 time points. In some embodiments, however, the 4D image set can include 2D image frames acquired at fewer or more positions and/or time points. Moreover, the individual 2D image frames are shown for illustrated purposes as two-dimensional grid. In other embodiments, however, the 2D frames can be presented in any suitable format. For example, in some embodiments, the ultrasound system may present one image or a portion of the images at a time.

Figure 8A:
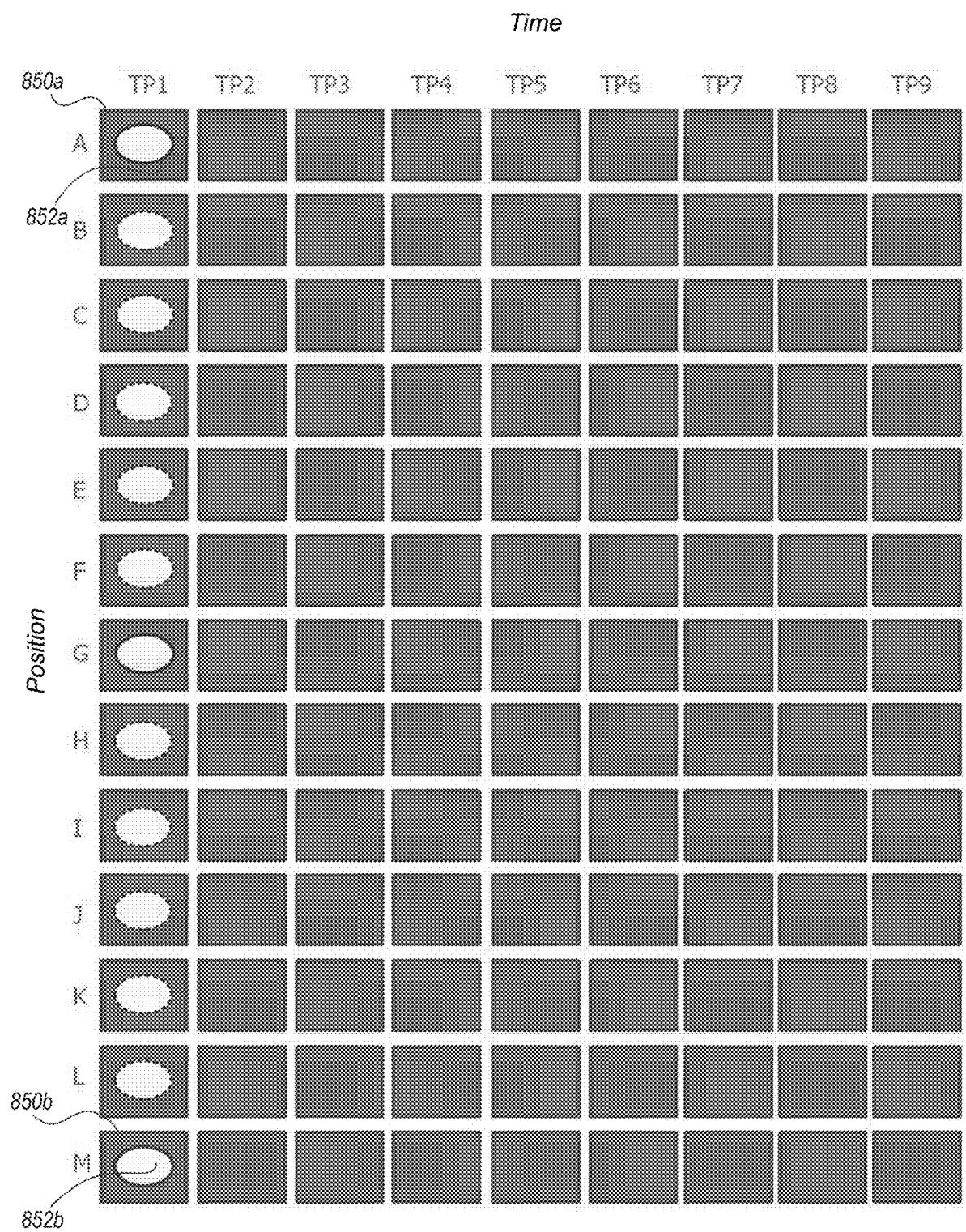
FIGS. 8A-8E are illustrations showing how the boundaries of anatomical structures are interpolated in accordance with some embodiments of the disclosed technology.

Referring now to FIG. 8A, an operator inputs points along a boundary of an anatomical structure in an image frame 850*a* and 850*b*. The ultrasound system (e.g., the system 131 of FIG. 1) draws corresponding boundaries 852*a* and 852*b* in the image on TP1 on frames 850*a* (TP1-A) and 850*b* (TP1-M), respectively. The ultrasound system then generates control points for the in-between frames TP1-B through TP1-L. The operator then modifies the position of any of the control points any in-between frames in accordance with the methods described above such that all the boundaries for this time point (TP1) suitably match the anatomical structure. For example, a user may modify the location of the control points in frame TP1-G to better coincide with the boundary of the anatomy captured in the ultrasound image. In some embodiments, the boundary may not start on TP1-A and finish on TP1-M but start and stop on other positions (e.g., the operator might begin placing control points on the image frame TP1-C and finish on TP1-K depending on the extents of the anatomical structure being traced).

Figure 8B:
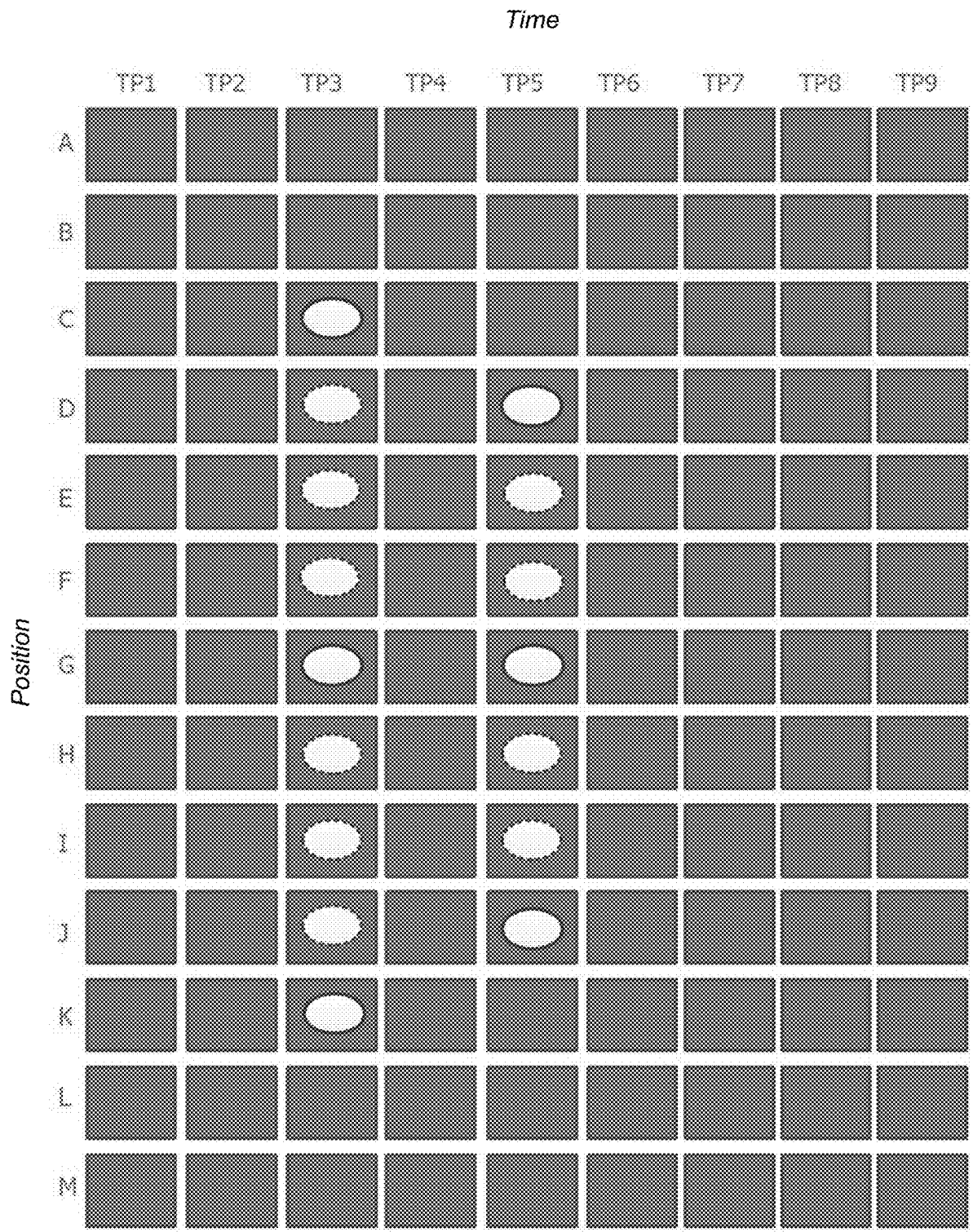

Referring now to FIG. 8B, the system then directs the user to draw completed boundaries for at least two image frames obtained at two additional time points; the ¼ position time point TP3 and the ½ position time point TP5. In other embodiments the ¼ and ½ time points will be different depending on how many total time points were used in performing a scan. The operator completes similar steps as described above to complete the trace for those time points. In some embodiments, the system automatically readjusts the display such the operator is presented only with image frames obtained at the ¼ time point for tracing. Once the image frames at the ¼ time points are complete, the system then moves to the ½ time point and instructs the user to complete the boundaries on at least two image frames obtained at this time point. After this has been completed, the user will have drawn complete boundaries for three time points TP1, TP3 (e.g. the ¼ position) and TP5 (e.g. the ½ position). The system will generate control point locations for the in-between frames based on those time points. For example, referring to FIG. 8B., TP3 D,E,F,H,I,J and TP5 E,F,H,I. The operator is not required to start the boundary trace on the first position (e.g. position A) and complete it on the last position (e.g. position M) but can start and stop on any two positions. If the anatomical structure is a heart, for example, it will compress in the middle of the cardiac cycle.

Figure 8C:
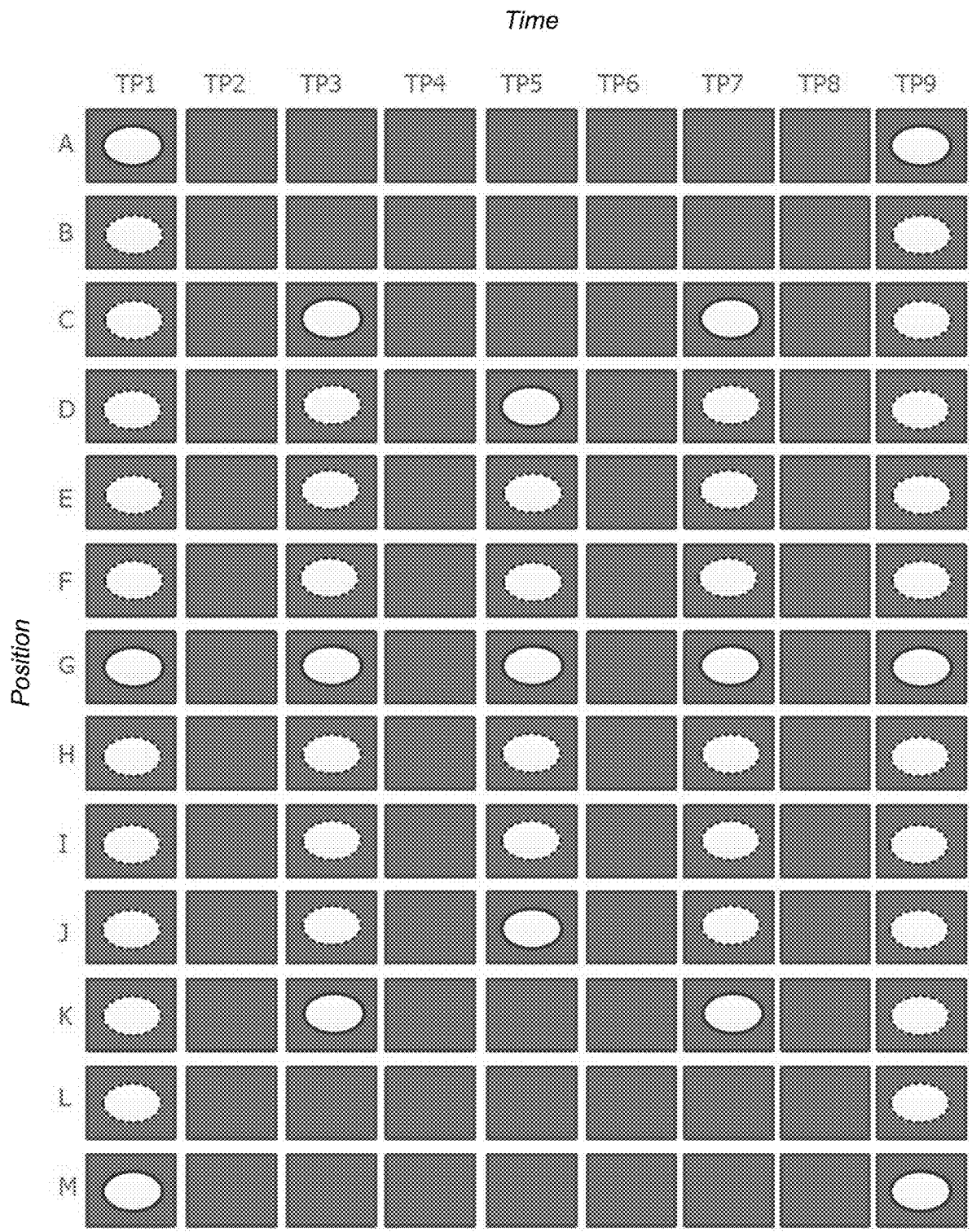

Referring now to FIG. 8C, as discussed above, for example, TP1 and TP9 occur when the heart is at a similar position in the subject's cardiac cycle. This means the boundary shape will also be similar. Also, data obtained at TP3 and TP7, referencing the ¼ and ¾ positions points in the subject's cardiac cycle will generally also result in similar boundary shapes. Accordingly, the boundary of the anatomical structure at similar portions of a subject's cardiac cycle can have the same or similar size and shape. In one embodiment, the system copies the boundaries from time TP1 to time TP9 and from TP3 to time TP7. In other embodiments, however, the operator may manually input the boundaries on frames obtained at times TP7 and TP9. The system will generate the data for the in-between frames for these time points.

Figure 8D:
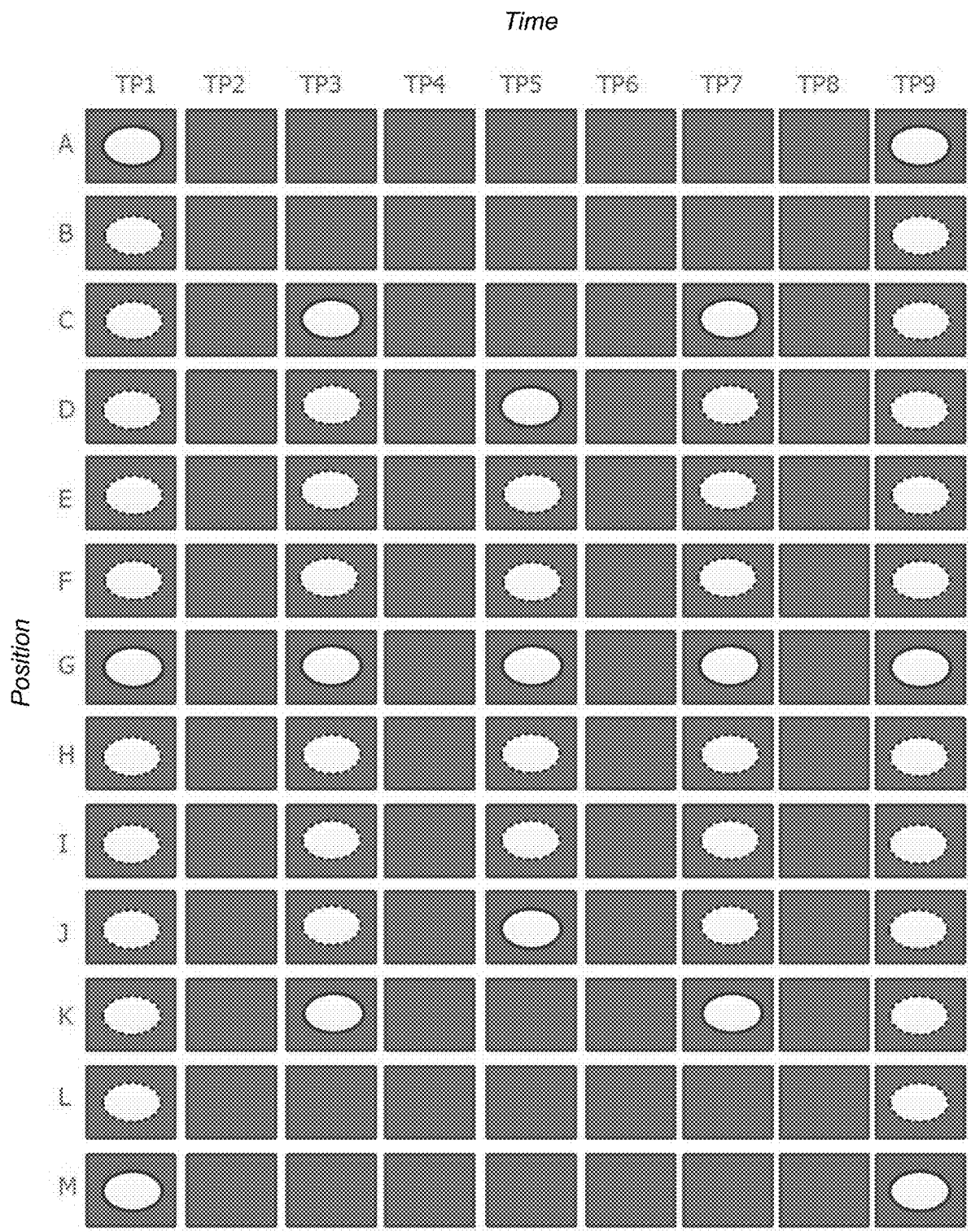

Referring now to FIG. 8D, the system then generates boundaries for all remaining time points which have not been either directly drawn by the operator (TP1, TP3, and TP5) or copied by the system from these existing boundaries (TP7 and TP9). These time points are referred to as "fixed time points" while the data for time points TP2, TP4, TP6, TP8 are generated by the system. These time points are referred to as "in-between time points". In some embodiments, depending on the number of total time points acquired, more in-between time points may exist. To generate a boundary for any frame obtained at an in-between time point, the system looks "horizontally" across different time points and interpolates data from two bounding frames obtained at the "fixed time points". For example, to generate a boundary for a frame TP2-F, the system interpolates from fixed frames TP1-F and TP3-F. This process in repeated for all frames on all in-between time points.

Figure 8E:
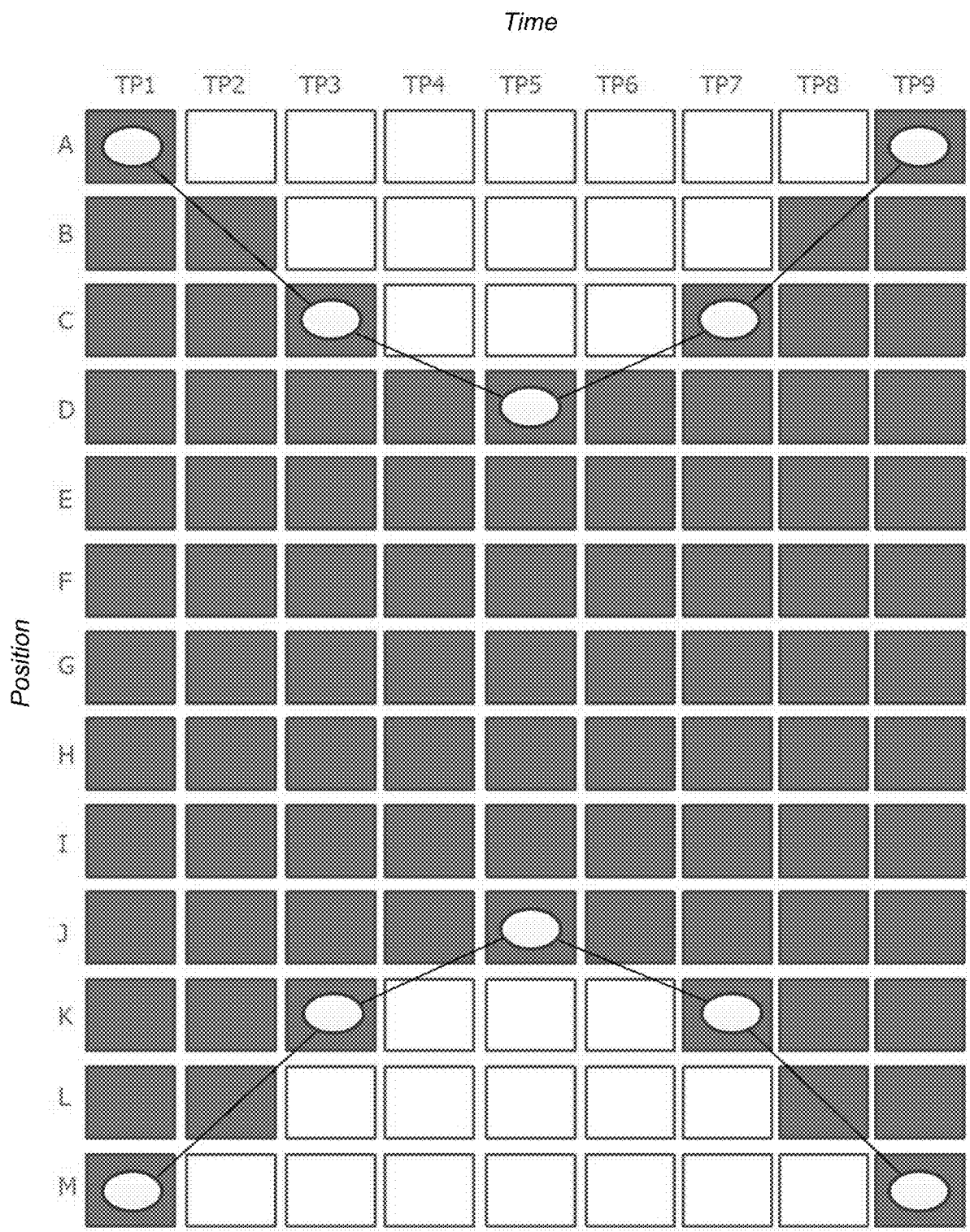

In some embodiments, the anatomical structure being traced, does not extend to the first and last acquired position for all time points. As with cardiac motion, the heart compresses as it nears the middle of the cardiac cycle. Thus the boundaries may only exist on a portion of the time point frames (e.g. in FIG. 8D, on TP5, the boundaries are drawn on frames TP5-D through TP5-J). When the system generates the boundaries for the in-between time points, a decision is made if a boundary exists on each frame based on the existence of bounding fixed frames. Referring to FIG. 8E, by joining the exterior bounding frames for each time point, a region mask can be formed differentiating which frames contain boundaries that are to be drawn and which do not. Frames outside this region (e.g. those drawn in white) do not receive a system generated in-between boundary. This region mask will change as the operator makes adjustments.

In some embodiments, image recognition software can analyze the 2D image frames and only display to the user those image frames for positions at which the anatomy can be seen. This can help the user enter control points for image frames that are used by the system to compute interpolated control points. Image frames at positions in which the anatomy does not extend can be hid from the user in order to reduce the number of image frames that the user has to view while inputting the control points.

The operator may now make adjustments to all in-between and fixed boundaries. Changes will result in updates to all in-between boundaries. For example, if the operator adjusts the fixed boundary in frame TP5-G (FIG. 8C), this would result in the boundaries of the bordering in-between frames of this time point being automatically updated by the system (e.g. TP5-E, TP5-F, TP5-H, TP5-I). Since this results in a change to position F, the other in-between time points would also be updated (e.g. TP4-F and TP2-F, TP6-F, TP8-F). As one can appreciate, this could result in global changes throughout all in-between frames. In one embodiment, to ensure the changes do not result in infinitely recursive updates, once a time point has been updated by the user (any frame on the time point) it will only update the boundaries of the frames in that time point "vertically". For example, in between frame TP5-E will only be interpolated based on frames in TP5 (e.g. TP5-D and TP5-G). Also, in-between time points (e.g. TP4) would only be interpolated "horizontally". For example, in-between frame TP4-E will only be interpolated based on frames in TP3 and TP5 (e.g. TP3-E and TP5-E). If a user makes an adjustment to any boundary on TP4, it ceases to be an in-between time point and becomes a fixed time point and is no longer interpolated "horizontally".

Figure 9:
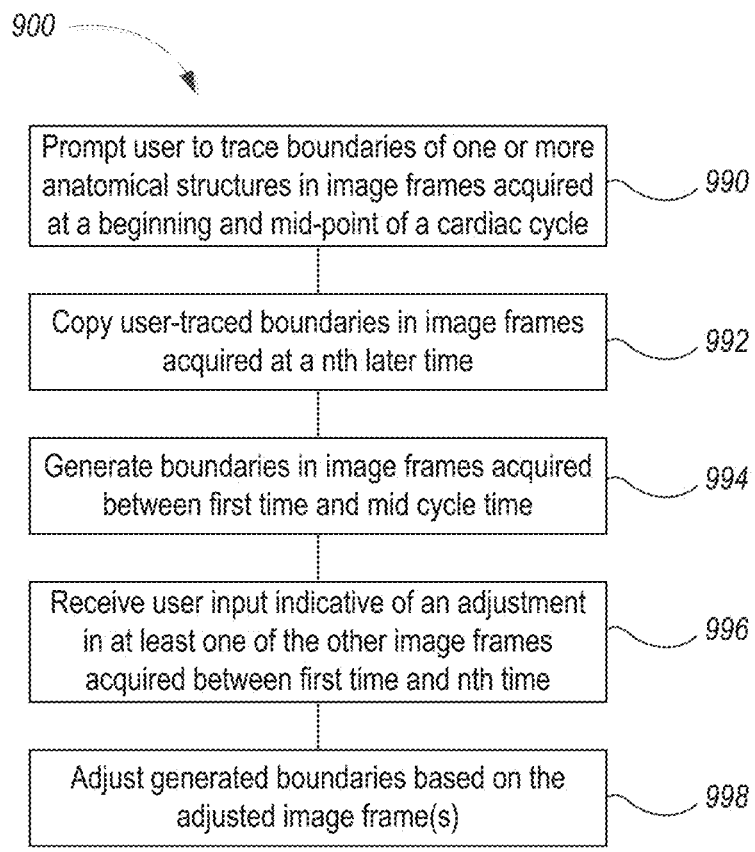
FIG. 9 is a flowchart of a process of generating boundaries of one or more anatomical structures in one or more ultrasound image frames in accordance with an embodiment of the disclosed technology.

FIG. 9 is a flowchart of a process 900 of generating boundaries of one or more anatomical structures in one or more 3D ultrasound images in accordance with an embodiment of the disclosed technology. At block 990, a user is prompted to trace the boundaries of an anatomical structure in a frame at the a first point in a cardiac cycle, at a second point that is generally a ¼ cycle later, and a third point that generally a half cycle later. At block 992, the process 900 copies the boundaries entered onto the first and ¼ image frame to a frame for an nth later time point that is approximately the same or a similar portion of the subject's cardiac cycle (e.g., time point TP1 to TP9 in FIGS. 8A-8E, and TP3 to TP7).

At block 994, the process 900 automatically generates boundaries in image frames acquired at a time after the first time point and the mid-cycle frame. Computed data can then be copied into frames at corresponding time periods in the cardiac cycle.

At block 996, the process 900 receives input indicative of an adjustment in the position of the control points one or more of the image frames generated at block 994. At block 998, the process 900 adjusts the boundaries in the remaining generated frames based on the adjustments at block 996. In some embodiments, the process 900 only adjusts frames acquired at the same position as the adjusted frames in block 996. In other embodiments, however, the process 900 adjusts all of the generated boundaries based on each boundary adjusted by the operator.

Conclusion

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the disclosed technology is not intended to be exhaustive or to limit the disclosed technology to the precise form disclosed above. While specific examples for the disclosed technology are described above for illustrative purposes, various equivalent modifications are possible within the scope of the disclosed technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the disclosed technology provided herein can be applied to other systems, not necessarily the system described above. The elements and acts of the various examples described above can be combined to provide further implementations of the disclosed technology. Some alternative implementations of the disclosed technology may include not only additional elements to those implementations noted above, but also may include fewer elements.

These and other changes can be made to the disclosed technology in light of the above Detailed Description. While the above description describes certain examples of the disclosed technology, and describes the best mode contemplated, no matter how detailed the above appears in text, the disclosed technology can be practiced in many ways. Details of the system may vary considerably in its specific implementation, while still being encompassed by the disclosed technology disclosed herein. As noted above, particular terminology used when describing certain features or aspects of the disclosed technology should not be taken to imply that the terminology is being redefined herein to be restricted to any specific characteristics, features, or aspects of the disclosed technology with which that terminology is associated. In general, the terms used in the following claims should not be construed to limit the disclosed technology to the specific examples disclosed in the specification, unless the above Detailed Description section explicitly defines such terms.

The invention claimed is:

1. A method of operating an ultrasound imaging system to determine a boundary of an anatomical structure in a subject, comprising:
   transmitting ultrasound energy from a probe having a transducer coupled to the ultrasound imaging system into the subject;
   acquiring ultrasound echo data from the subject using the transducer;
   displaying, with the ultrasound imaging system, a plurality of two-dimensional (2D) image frames of a region of interest in the subject using the acquired ultrasound echo data;
   receiving user input at a user interface of the ultrasound imaging system, wherein the user input includes user-selected control points in at least a first and second image frame defining boundaries of the anatomical structure at different points in time and wherein the at least first and second image frames are acquired at different positions relative to the region of interest by moving the probe;
   automatically generating internal points along the boundaries of the anatomical structure between the user-selected control points in the at least first and second image frames;
   automatically generating control points corresponding to the user-selected control points in at least one intermediate image frame, wherein the at least one intermediate image frame is obtained at a time between the first and second image frame and at the different positions relative to the regions of interest;
   interpolating the user-selected control points and internal points onto the at least one intermediate image frames to determine boundaries of the anatomical structure in the intermediate image frames;
   computing a boundary of the anatomical structure in at least one of the first and second image frame and the at least one intermediate frame from at least one of the user-selected control points, the internal points, and the automatically generated control points, and copying the boundary from an image frame obtained at a first point in a cardiac cycle to an image frame obtained at a second point in the cardiac cycle that is separated by the first point by one half of the cardiac cycle; and
   displaying to a user only those 2D ultrasound frames in which the anatomical structure is visible and hiding 2D ultrasound image frames in which the anatomical structure is not visible.

2. The method of claim 1, wherein the anatomical structure varies in size over a cardiac cycle, and wherein the method further comprises:
   displaying a number of 2D image frames in which a maximum and minimum size of the anatomical structure can be seen at various positions in the region of interest for a time during the cardiac cycle.

3. The method of claim 1, further comprising displaying a number of 2D image frames in which a maximum and minimum size of the anatomical structure can be seen at various positions in the region of interest for a time during the cardiac cycle.

4. The method of claim 1, wherein the ultrasound energy has a center frequency greater than or equal to about 20 MHz.

5. The method of claim 1, further comprising:
   receiving user-selected points in a third image frame that forms a boundary of the anatomical structure in the third image frame,
   wherein the third image frame includes ultrasound echo data acquired at a position and a time, and
   wherein the second image frame is acquired at a time between the times at which the first and third image frames are acquired.

6. The method of claim 5, wherein the interpolating is weighted based on at least one of distances between the second position and the first and third positions, respectively, and differences in times between the second time and the first and third times, respectively.

7. The method of claim 1, further comprising moving the probe along two or more axes.

8. An ultrasound imaging system to determine a boundary of an anatomical structure in a subject, comprising:
   an ultrasound probe having a transducer configured to transmit ultrasound energy into a subject and acquire ultrasound echo data from the subject;
   a processor configured to:
   display a plurality of two-dimensional (2D) image frames of a region of interest in the subject using the acquired ultrasound echo data;
   receive user input of user-selected control points for at least a first and second 2D image frame defining boundaries of an anatomical structure at different points in time and at different positions relative to the region of interest, wherein the different positions are achieved by moving the probe;
   automatically generate internal points along the boundaries of the anatomical structure between the user-selected control points in the at least first and second image frames;
   automatically generate control points corresponding to the user-selected control points in at least one intermediate image frame, wherein the at least one intermediate image frame is obtained at a time between the first and second image frame and at the different positions relative to the regions of interest;
   interpolate the user-selected control points and internal points onto the at least one intermediate image frames to determine boundaries of the anatomical structure in the intermediate image frames;

compute a boundary of the anatomical structure in at least one of the first and second image frame and the at least one intermediate frame from at least one of the user-selected control points, the internal points, and the automatically generated control points, and copy the boundary from an image frame obtained at a first point in a cardiac cycle to an image frame obtained at a second point in the cardiac cycle that is separated by the first point by one half of the cardiac cycle; and display to a user only those 2D ultrasound frames in which the anatomical structure is visible and hide 2D ultrasound image frames in which the anatomical structure is not visible.

9. The system of claim 8, wherein the anatomical structure varies in size over a cardiac cycle and the processor is configured to display a number of 2D image frames in which a maximum and minimum size of the anatomical structure can be seen at various positions in the region of interest for a time during the cardiac cycle.

10. The system of claim 8, wherein the ultrasound energy has a center frequency greater than or equal to about 20 MHz.

11. The system of claim 8, wherein the probe is moved along two or more axes.

12. A method of operating an ultrasound imaging system to determine a volume of a region of interest in a subject, comprising:

acquiring ultrasound echo data from the subject using a transducer coupled to the ultrasound imaging system, wherein the ultrasound echo data is acquired at a plurality of times and at a plurality of positions relative to the region of interest;

constructing, with the ultrasound echo data, a plurality of two-dimensional image frames of the region of interest, wherein at least two of the plurality of image frames are non-parallel;

constructing, with the ultrasound imaging system, a plurality of three-dimensional (3D) images of the region of interest in the subject using the image frames, wherein individual 3D images of the plurality of 3D images comprise a plurality of image frames and wherein each image frame is acquired at one of the plurality of positions and at one of the plurality of times;

receiving manual input at a user interface of the ultrasound imaging system, wherein the manual input includes user-selected points in a first image frame of the plurality of image frames along a user-defined boundary of the region of interest in the first image frame, and wherein the first image frame includes ultrasound echo data acquired at a first position and a first time;

generating a boundary of the region of interest in at least a second image frame based on the user-selected points in the first image frame, wherein the second image frame includes ultrasound echo data acquired at a second position and a second time; and calculating, based on a plurality of boundaries of the region of interest in at least the first and second image frame, the volume of the region of interest.

13. The method of claim 12, further comprising:

receiving user-selected points in a third image frame of the plurality of image frames that form a boundary of the region of interest in the third image frame, wherein the third image frame includes ultrasound echo data acquired at a third position and a third time, and wherein the second time is between the first and third times.

14. The method of claim 13 wherein generating the boundary of the region of interest in the second image frame further comprises:

interpolating the user-selected points onto image frames obtained between the first and third image frames; and connecting adjacent ones of interpolated points in the second image frame with a cubic spline.

15. The method of claim 14 wherein the interpolating is weighted based on distances between the second position and the first and third positions, respectively.

16. The method of claim 14 wherein the interpolating is weighted based on differences in times between the second time and the first and third times, respectively.

17. The method of claim 12 wherein the ultrasound energy has a center frequency greater than or equal to about 20 MHz.

18. The method of claim 12 wherein the individual 3D images are representative of corresponding different portions of a heart during a subject's cardiac cycle.

19. The method of claim 12 further comprising automatically generating internal points along the user-defined boundary of the region of interest between the user-selected points in the first image frame, wherein the boundary of the region of interest in the at least the second image frame is further based on the internal points in the first image frame.

20. The method of claim 12 further comprising automatically generating, in at least the second image frame, control points corresponding to the user-selected control points in the first image frame, wherein the boundary of the region of interest in the at least second image frame is further based on the automatically generated control points.

* * * * *